United States Patent [19]

Filley

[11] 4,388,918
[45] Jun. 21, 1983

[54] MENTAL HARMONIZATION PROCESS

[76] Inventor: Charles C. Filley, 1207 Saxony La., Houston, Tex. 77058

[21] Appl. No.: 270,904

[22] Filed: Jun. 5, 1981

[51] Int. Cl.$^3$ ............................................. A61B 19/00
[52] U.S. Cl. ................................. 128/1 C; 179/1 AA
[58] Field of Search ..................... 128/1 C; 179/1 AA

[56] References Cited

U.S. PATENT DOCUMENTS

| | | | |
|---|---|---|---|
| 2,843,111 | 7/1958 | Roll | 128/1 C |
| 3,014,477 | 12/1961 | Carlin | 128/1 C |
| 3,213,851 | 10/1965 | Currea | 179/1 AA |
| 3,272,198 | 9/1966 | Balkin | 179/1 AA |
| 3,773,049 | 11/1973 | Rabichev et al. | 128/1 C X |
| 4,289,121 | 9/1981 | Kuprinanovich | 128/1 C |
| 4,315,502 | 2/1982 | Gorges | 128/1 C |

*Primary Examiner*—Kyle L. Howell
*Assistant Examiner*—John C. Hanley
*Attorney, Agent, or Firm*—Russell H. Schlattman

[57] ABSTRACT

A state of relaxation or mental harmonization in a subject is created by exposing a color solely to one field of vision of a subject and the complement of that color solely to the other field of vision of the subject while simultaneously exposing an audible tone solely to one ear of the subject and a harmonious tone solely to the other ear of the subject. The color and tones employed are subjectively comfortable and compatible. Preferably, the frequency difference between the two audible tones is one-half the frequency of the audible tone having the lowest frequency.

2 Claims, No Drawings

MENTAL HARMONIZATION PROCESS

FIELD OF THE INVENTION

This invention is concerned with a process of producing a state of mental harmonization or relaxation in a subject through a novel use of visible colors and audible tones.

DESCRIPTION OF THE PRIOR ART

The use of visual and audio stimuli to induce sleep, create hypnotic or anesthetic states in a subject, or for the treatment of various neuropsychic and somatic diseases is well known in the art. U.S. Pat. No. 3,576,185 discloses the use of modulated sound and light to induce sleep. U.S. Pat. No. 3,773,049 employs a combination of heat, light, sound and VHF electromagnetic radiation for treatment of neuropsychic and somatic diseases. U.S. Pat. No. 3,884,218 discloses a method of inducing sleep through the generation of audio signals which are produced by the modulation of familiar repetitive noises with EEG sleep patterns. U.S. Pat. No. 3,885,998 discloses an entertainment device wherein a user's response to visual and audio stimuli are measured and the results thereof used to modify the stimuli to maximize a desired response. U.S. Pat. No. 4,191,175 employs repetitive noise-like signals in combination with repetitive visual signals for changing states of consciousness.

The methods of the prior art have much merit in creating a state of mental relaxation or harmonization. However, effective results are achieved by the much simpler technique of this invention which subjects selected portions of the brain to separate externally generated stimulii.

DISCLOSURE OF THE INVENTION

The neocortex portion of the human brain is composed of two major hemispheres, right and left. These hemispheres, connected by a bridge denoted as the corpus callosum, on ocassion do not act in cooperation with one another. Cases of severe epilepsy, for instance, have been found to be the result of electrical storms between the two hemispheres.

The hemispheres of the brain are, in effect, cross connected to opposing sides of the body. Hence, specific sound information introduced to the left ear will be transmitted along nerve trains to the right hemisphere of the neocortex and conversely, sound transmitted through the right ear will ultimately reside in the left hemisphere. Similarly, color information observed through the left eye will be sent to the right hemisphere and data from the right eye will be registered in the left hemisphere.

The object of the present invention is to bring about a balance, or more harmonious relationship, between the two hemispheres of the brain through the creation of externally generated harmonious energy fields and subsequent exposure of each hemisphere of the brain to the respectively separately generated energy fields. The energy fields employed in this invention are sound and light. While harmonious energy relationships may be produced by either sound or light, this invention employs the simultaneous use of both in order to bring about an alignment of the subject as well as balanced inter-hemisphere activity.

The method of the present invention comprises, in combination, the steps of exposing solely to one field of vision (FOV) of a subject a first color while simultaneously exposing solely to the other FOV of the subject the complementary color of said first color and exposing to one ear of the subject a first audible tone subjectively compatible with the color in the FOV corresponding to said ear while simultaneously exposing to the other ear of the subject a second audible tone which is harmonious with said first audible tone and subjectively compatible with the color exposed to the FOV corresponding to said other ear.

Considering first the color stimuli, it is well known that all colors in the visible spectrum arouse the activity of their complement. If one stares at red for several minutes and then removes his vision to a neutral background, red's complement, green, will be observed. In such an instance the brain is compensating for the simulation in an attempt to return to a neutral gray state. The following table is a simplified listing of hues in the visible spectrum with the hues set forth in one column being complementary to the hues oppositely set forth in the other column.

| | |
|---|---|
| RED | GREEN |
| RED-ORANGE | BLUE-GREEN |
| ORANGE | BLUE |
| YELLOW-ORANGE | BLUE-VIOLET |
| YELLOW | VIOLET |
| YELLOW-GREEN | RED-VIOLET |
| GREEN | RED |
| BLUE-GREEN | RED-ORANGE |
| BLUE | ORANGE |
| BLUE-VIOLET | YELLOW-ORANGE |
| VIOLET | YELLOW |
| RED-VIOLET | YELLOW-GREEN |

The complementary relationship between colors can be somewhat more precisely stated in terms of the frequency of the repeating wave length patterns in the visible color spectrum. The frequency of visible light or color ranges from $400 \times 10^{12}$ cycles per second (cps) at the infrared end of the spectrum to approximately $800 \times 10^{12}$ cps at the ultraviolet end of the spectrum. Two colors can be said to be complementary of each other when the difference in their frequencies is approximately one half the frequency of the color having the lower frequency.

In the practice of this invention, complemetary hues, those in opposition to one another, would be used in matched pairs. One hue will be offered to the left FOV and the other to the right FOV. Within the spectrum of visible light, hues near the infrared end have a tendency to stimulate brain wave activity while those toward the ultraviolet end tend to act as a sedative. Thus, if red is selected for use and applied to the left FOV, then green will be selected for application to the right FOV. The right hemisphere is then stimulated in its activity while the left is sedated.

The audible tones used should be compatible to the color combinations selected. This is accomplished by having the subject select an audible tone for one ear that is comfortable and pleasing to him while viewing the previously selected color in the FOV corresponding to that ear. It is known that people can relate certain sounds to certain colors. For example, when relating two audible tones of different frequencies to a particular color, some people will associate the lower frequency audible tone to colors tending toward the ultraviolet end of the visible spectrum and relate the higher frequency audible tone to colors tending toward the infrared region of the visible spectrum. Others may sense an opposite relationship. The audible tone subjected to the other ear of the subject should be harmonious with said first audible tone and at the same time be comfortable and pleasing to him while viewing the color in the FOV corresponding to that ear. While many harmonious combinations of tones can be selected, it is preferred that the frequency difference between the two audible tones be one-half the frequency of the audible tone having the lowest frequency, thereby being compatible with the frequency difference between the two colors being employed.

DESCRIPTION OF THE PREFERRED EMBODIMENT

According to the preferred embodiment of this invention, the subject to be treated selects a color from the visible spectrum that is particularly comfortable or pleasing to him. This color is then placed so that it is exposed solely to either his right or left FOV. The complement of that color is then exposed solely to the other FOV. The FOV for the color and the FOV for its complement is selected by the subject in accordance to that which is most comfortable and pleasing to him. The intensity of the color and its complement is adjusted to provide a subjective balance and comfort between the two.

While observing the color and its complement in the respective FOV an audible tone is generated in one ear of the subject and its frequency adjusted until it is subjectively comfortable and compatible with the color in the FOV corresponding to that ear. A harmonious tone is then generated solely in the other ear of the subject with the frequency adjusted such that it is subjectively comfortable and compatible with the first mentioned tone and the color observed in the FOV corresponding to the other ear and the frequency difference between the two audible tones is one-half of the frequency of the audible tone having the lower frequency. The intensity of the two tones are adjusted for subjective balance and comfort.

The subject is then continuously exposed to the two audible tones while simultaneously viewing the two colors in their respective FOV. The time of exposure is subjectively determined by the subject, the time being that which is necessary to move the subject toward a feeling of relaxation or lessened anxiety. The time can vary from as little as a few minutes to as much as thirty minutes or more and can be repeated at intervals as determined by the subject.

In practicing the method of this invention, it is important that the right and left FOV be substantially isolated from each other so that the matched hues can be viewed individually in the respective FOV without crossover to the other. This can be accomplished by any technique well known to those skilled in the art. A particularly simple but effective method employs the use of close fitting, wrap around goggles, with the lenses of the goggles being optical filters of the desired hues. The hues can then be viewed by looking through the goggles against an illuminated white or neutral background.

In the case of the two audible tones utilized in the practice of this invention, it is equally important that the tone subjected to one ear of the subject not cross over to the other ear. This too can be accomplished by techniques and methods well known to those skilled in the art. The tones can be generated by any of the equipment readily available and commonly used in the practice of audiometric testing. A tone can be individually fed to each ear through the use of conventional earplugs or ear muffs in the manner commonly employed for stereo reception.

While the beneficial end results of the practice of the method of this invention is primarily a subjective determination, conventional encephalographic measurements on the subject before, during and after treatment can be used to provide a more precise scientific measurement of the effects obtained.

What is claimed is:

1. Method of producing a state of mental relaxation in a subject, comprising, in combination, the steps of:
 (a) exposing solely to one field of vision of the subject a first color determined by the subject to be pleasing to him while simultaneously exposing solely to the other field of vision of the subject the complementary color of said first color; and
 (b) exposing solely to one ear of the subject a first audible tone determined by the subject to be pleasing to him while simultaneously exposing solely to the other ear of the subject a second audible tone harmonious with said first audible tone; and
 (c) said colors being viewed by the subject while simultaneously listening to said audible tones.

2. The method of claim 1 wherein the first and second audible tones have a frequency difference of approximately one-half the frequency of the audible tone having the lowest frequency.

* * * * *